United States Patent [19]  [11] 3,968,176
Uehama et al.  [45] July 6, 1976

[54] PROCESS FOR PRODUCING PENTAERYTHRITOL

[75] Inventors: Hiromi Uehama; Kei Hioki, both of Takaishi; Akira Onuki, Mohara; Kazuo Hirokawa; Takeshi Shoji, both of Yokohama, all of Japan

[73] Assignee: Mitsui Toatsu Chemicals, Incorporated, Tokyo, Japan

[22] Filed: July 3, 1975

[21] Appl. No.: 593,125

[30] Foreign Application Priority Data
July 5, 1974  Japan.............................. 49-76406

[52] U.S. Cl........................... 260/637 P; 260/635 P
[51] Int. Cl.²................... C07C 27/26; C07C 29/24
[58] Field of Search................................ 260/637 P

[56] References Cited
UNITED STATES PATENTS

| | | |
|---|---|---|
| 2,223,421 | 12/1940 | Hubacher et al................ 260/637 P |
| 2,939,887 | 6/1960 | Maury et al..................... 260/637 P |
| 2,978,514 | 4/1961 | Poynton .......................... 260/637 P |
| 3,066,171 | 11/1962 | Clunie et al..................... 260/637 P |

FOREIGN PATENTS OR APPLICATIONS

| | | |
|---|---|---|
| 576,266 | 5/1959 | Canada........................... 260/637 P |
| 799,182 | 8/1958 | United Kingdom............. 260/637 P |
| 1,035,103 | 7/1966 | United Kingdom............. 260/637 P |

Primary Examiner—Joseph E. Evans
Attorney, Agent, or Firm—Fisher, Christen & Sabol

[57] ABSTRACT

A process for producing pentaerythritol wherein at least part of a reaction solution which contains pentaerythritol formals is thermally treated in a pH range of 4.5–5.5 at a temperature of 120°–170°C. for 20–120 minutes and the resultant pentaerythritol is separated as crystals. Sodium hydroxide is added to the separated solution to cause sodium formate to crystallize, followed by separation of the crystals. The remaining solution is recirculated to the reaction system for use in the starting reaction solution.

3 Claims, 1 Drawing Figure

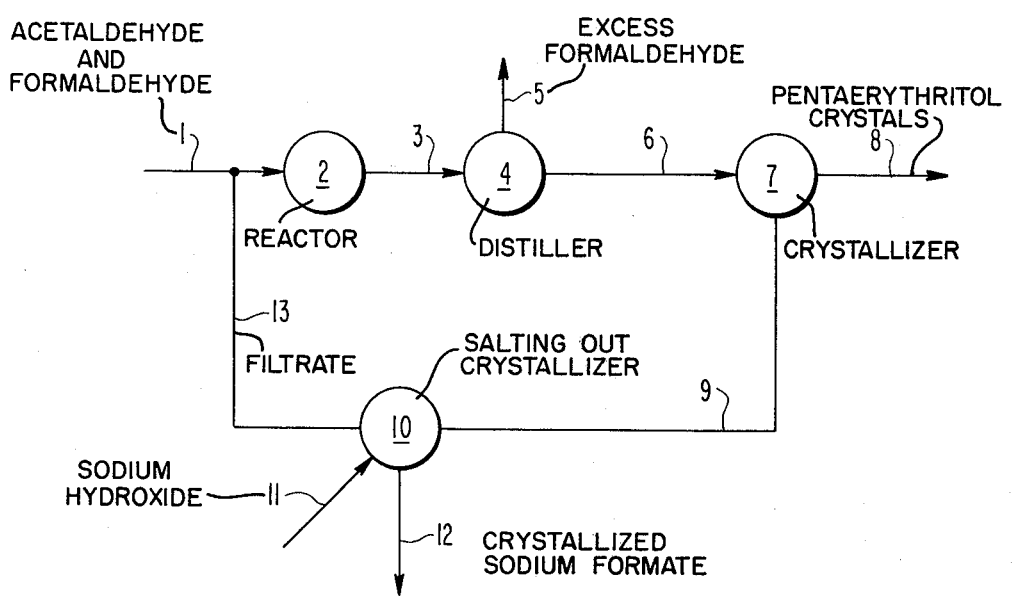

3,968,176

PROCESS FOR PRODUCING PENTAERYTHRITOL

FIELD OF THE INVENTION

This invention relates to improvements in a process for producing pentaerythritol by reacting acetaldehyde with formaldehyde in a sodium hydroxide aqueous solution and, more particularly, to an improved process for producing pentaerythritol wherein sodium hydroxide is added to an aqueous solution of sodium formate formed during the course of formation of pentaerythritol to separate sodium formate by crystallization and the remaining separated solution is recirculated to the reaction system for use in the starting reaction solution.

BACKGROUND OF THE INVENTION

The interaction of acetaldehyde and formaldehyde in a sodium hydroxide aqueous solution results in formation of an equimolar sodium formate as well as pentaerythritol. This sodium formate must be separated from the pentaerythritol in an efficient manner. In general, the reaction solution is condensed and cooled for separation into solid pentaerythritol containing only a small amount of sodium formate and a condensed solution of liquid pentaerythritol which contains a relatively large amount of sodium formate. The solid pentaerythritol can be converted by a simple operation into pentaerythritol crystals with high purity. However, it is difficult to separate pure pentaerythritol crystals from the condensed solution containing a large content of sodium formate and it is uneconomical to discard the condensed solution as it is.

DESCRIPTION OF THE PRIOR ART

A number of methods have been proposed to collect pentaerythritol from the above-described condensed solution, including the process of Japanese Patent Publication No. 18008/1971, assigned to the assignee of the present invention, wherein a strong base, e.g., sodium hydroxide, which has cations common to those of the formate is added to the condensed solution of pentaerythritol for separating the formate as crystals, and the resultant solution which contains pentaerythritol and the strong base is recirculated to the reaction system for use as a starting material for the preparation of pentaerythritol. Sodium formate similarly to pentaerythritol is very soluble in water and also has a great dissolving power for pentaerythritol. However, when a compound having ions common to those of the formate is added to the condensed solution as in the above process, the formate, e.g., sodium formate, is crystallized at high purity by the salting-out action of the common ions, and the process is very useful industrially. However, this process often involves an unfavorable phenomenon when the recovered solution is repetitively employed as a starting material in preparation of pentaerythritol. That is, pentaerythritol formals which are by-products are much more difficult to crystallize when compared with pentaerythritol, and are accumulated in the alkali aqueous solution during repetitive use as a pentaerythritol-synthesizing starting material. The pentaerythritol formals not only lower the yield of pentaerythritol, but also tend to be formed into fine crystals, and when existing in an aqueous solution in large amount, they serve to also render the pentaerythritol crystals much finer and to lower the rate of crystallization of pentaerythritol. Thus the resultant pentaerythritol crystals disadvantageously become low in purity. In addition, the lowering in purity is even further facilitated by repetitively circulating a large amount of the pentaerythritol formals to the step of synthesizing pentaerythritol since the formals are gradually converted into three-dimensional pentaerythritol formals with greater average degrees of polymerization. Representative of pentaerythritol formals are bispentaerythritol and pentaerythritol monocyclicformal. It is well known that these formals can be decomposed into pentaerythritol by various methods.

For example, U.S. Pat. No. 2,978,514 describes a process wherein an aqueous solution containing pentaerythritol formals is thermally treated for decomposition at its boiling point under normal pressure in the presence of a strong acid such as sulfuric acid, hydrochloric acid or the like. However, this process is disadvantageous in that the decomposition should be effected at a relatively low temperature of 95°–105°C. for suppressing the further side reaction of the employed strong acid with formed pentaerythritol, thus lowering the decomposition rate. Further, U.S. Pat. No. 2,939,887 teaches a process of thermally treating pentaerythritol formals for decomposition at a temperature as high as 150°–300°C. in the presence of a silicabase catalyst for petroleum cracking. However, this process has the disadvantage that the operation is complicated due to the use of the solid catalyst. In addition, Japanese Patent Publication No. 18107/1964 describes a process wherein formaldehyde and acetaldehyde are interacted under specific conditions whereby pentaerythritol formals are produced in large amount, and then the formals are subjected to decomposition under severe conditions such as of a pH of 3–4 and a temperature of 150°–200°C. However, this process disadvantageously requires a large amount of a pH adjuster and a high installation cost to prevent corrosion of the installation material.

SUMMARY OF THE INVENTION

It is an object of the present invention to provide a process for producing pentaerythritol wherein sodium hydroxide is added to an aqueous solution containing pentaerythritol and sodium formate to separate the sodium formate by crystallization and the separated solution is recirculated to the reaction system for use as part of a starting reaction solution, the pentaerythritol formals which are accumulated in the reaction system being readily decomposed into pentaerythritol under relatively moderate conditions.

It is another object of the present invention to provide a process for producing pentaerythritol wherein highly pure pentaerythritol is obtained in a stable crystal form at a high rate of crystallization by a simple crystallization and separation operation by suitably controlling the amount of accumulated pentaerythritol formals which would have an adverse effect on the rate of crystallization and the crystal form.

In accordance with the present invention, there is provided a process for producing pentaerythritol wherein sodium hydroxide is added to an aqueous solution containing pentaerythritol and sodium formate to separate sodium formate as crystals and the remaining solution is recirculated for use as part of the starting reaction solution. The process comprises thermally treating at least part of a reaction solution containing pentaerythritol formals in the pH range of 4.5–5.5 at a temperature of 120°–170°C. for 20–120 minutes, separating the pentaerythritol by crystallization, adding sodium hydroxide to the separated solution containing liquid or remaining pentaerythritol and sodium formate for separating the sodium formate as crystals, whereby the pentaerythritol formals can be easily decomposed into pentaerythritol and pentaerythritol is obtained in an efficient manner.

Furthermore, the crystals of pentaerythritol can be obtained more efficiently by controlling the content of pentaerythritol formals in the solution obtained after the separation of pentaerythritol to less than 3.0 wt. %, expressed in terms of the combined formaldehyde concentration.

The usually employed reaction conditions under which acetaldehyde and formaldehyde are interacted with each other to form pentaerythritol, including reaction temperature, reaction time, molar ratio of formaldehyde to acetaldehyde, molar ratio of water to acetaldehyde, molar ratio of sodium hydroxide to acetaldehyde, and the like, may be used as such in the process of the invention.

BRIEF DESCRIPTION OF THE DRAWING

The sole FIGURE is a flow chart showing the production of pentaerythritol in accordance with the process of the present invention.

DESCRIPTION OF THE PREFERRED EMBODIMENTS

As described above, the process of the present invention is characterized by separating pentaerythritol as crystals from the reaction solution, adding sodium hydroxide to the resultant aqueous solution containing the remaining pentaerythritol and sodium formate for separating the sodium formate therefrom in the form of crystals, and recirculating the separated solution containing an excess of sodium hydroxide to the reaction solution for use as part of the starting reaction solution. The separated solution to be recirculated generally contains sodium formate, pentaerythritol, pentaerythritol formals and polypentaerythritol as well as an excess of sodium hydroxide.

The reaction solution which is obtained as the result of reaction of fresh formaldehyde and acetaldehyde and which contains the recirculated solution contains freshly formed pentaerythritol, the circulated impurities, freshly formed impurities including pentaerythritol formals, and a great excess of unreacted formaldehyde. In general, the great excess of unreacted formaldehyde is removed by pressure distillation.

In the process of the present invention, it is essential to thermally decompose the pentaerythritol formals contained in the reaction solution, for example, at the bottom of a pressure distilling column or in a vessel into which the reaction solution is discharged through the bottom of the pressure distilling column, and then to allow pentaerythritol to crystallize for separation. Prior to the thermal treatment of pentaerythritol formals in the reaction solution, the pH of the solution should be adjusted to 4.5–5.5. The thermal decomposition is readily feasible at a temperature of 120°–170°C. for a time period of 20–120 minutes.

As described above, any pH value may be used within the range of 4.5–5.5 for decomposition of pentaerythritol formals. When the pH is greater than 5.5, the decomposition efficiency becomes extremely poor, while pH conditions of less than 4.5 undesirably present economical problems since a larger amount of formic acid and an installation material with higher quality are required.

With a decomposition temperature below 120°C. in the pH range of 4.5–5.5, the decomposition rate of pentaerythritol formals becomes extremely low, it being almost impossible to decompose the pentaerythritol formals at a high rate even when the formals are contained in a relatively high concentration, so that the purity of the product will be lowered as in the aforementioned prior process. On the other hand, the use of a decomposition temperature of greater than 170°C. is not advantageous since an ordinary heat source can not be utilized.

With lower decomposition temperatures, a longer time period is necessitated to increase the decomposition rate. Within the above-mentioned temperature range, the decomposition time is generally within the range of 20–120 minutes, preferably 50–100 minutes.

Upon decomposition of the pentaerythritol formals by the thermal treatment, the decomposition rate is preferably maintained below 3.0 wt. % when expressed in terms of the content of pentaerythritol formals in the solution obtained after the separation of pentaerythritol by crystallization, i.e., the concentration of combined formaldehyde in the separated solution. More preferably, the combined formaldehyde concentration of the solution is kept below 2 wt. %.

The term "pentaerythritol formals" as herein used is intended to mean acetal compounds of pentaerythritol and formaldehyde. The content of pentaerythritol formals is intended to mean the concentration of combined formaldehyde in the separated solution, the content of formaldehyde combined with pentaerythritol being determined by the usual chromotropic acid method, as particularly described, for example, in the Industrial & Engineering Chemistry, Vol. 17- 400–402 (1945).

By controlling the combined formaldehyde concentration of the solution, for example, below 2 wt. %, the concentration of pentaerythritol in the separated solution, for example, at 40°C., may be maintained in a relatively low range below 20 wt. %, thus making it possible to crystallize pentaerythritol at a high rate. In this connection, however, when the combined formaldehyde concentration of the separated solution is greater than 3.0 wt. %, the concentration of pentaerythritol in the separated solution will be increased up to above 30 wt. %, lowering the crystallization rate a considerable extent.

In general, the combined formaldehyde concentration of the separated solution has a great effect on the crystal habit of the resultant pentaerythritol crystals. That is, when the combined formaldehyde concentration is increased, pentaerythritol is crystallized into fine single crystals without forming mimetic crystals which are larger in size, presenting many problems in handling and quality of the crystals. The term "mimetic crystals" herein used is intended to mean a lump of large-sized crystal particles in the form of a chrysanthemum or confetti which is composed of a number of minute crystals, and the mimetic crystals are clearly distinguished from single crystals in a chemical sense.

When the separated solution in which the combined formaldehyde concentration is kept below 2 wt. % is subjected to crystallization at 40°C. by the use of an ordinary continuous vacuum adiabatic cooling crystallizer, pentaerythritol is obtained in the form of mimetic crystals with a size as large as 100–300 $\mu$, being easily separable by usual methods. On the contrary, when the separated solution with a combined formaldehyde concentration of greater than 3 wt. % is subjected to crystallization in the manner described above, pentaerythritol is formed into fine single crystals with a size of 10–50 $\mu$, and separation of the crystals from the solution requires a great deal of labor.

As will be understood from the foregoing, the process of the present invention has several advantages when the crystallization and separation operations are effected by controlling the amount of pentaerythritol formals in the solution obtained after the crystallization and separation operations below 3.0 wt. %, preferably below 2.0 wt. %, expressed in terms of the combined formaldehyde concentration.

One of the advantages of the invention is that the crystals of pentaerythritol obtained by the crystallization and separation have a large size, being easily separable from the solution by a simple separation operation.

Another advantage of the invention is that the pentaerythritol concentration of the solution obtained after the crystallization and separation of pentaerythritol is low, i.e., pentaerythritol is obtained at a high rate of crystallization, and the separated solution is low in viscosity and therefore easy to handle.

A further advantage of the invention resides in that the pentaerythritol concentration of the separated solution is low, so that it is possible to raise the crystallization rate of sodium formate and the operation in the crystallization system is facilitated.

A still further advantage of the invention is that pentaerythritol with high purity can be obtained at a good yield.

It is well known that maintenance of the pH value of a pentaerythritol formal-containing solution as low as possible is advantageous in increasing the rate of decomposition of the pentaerythritol formals. However, the formal-containing solution also contains a large amount of sodium formate, so that a large amount of formic acid will be necessitated due to the buffer action of sodium formate in order to lower the pH of the solution a considerable extent.

In the present invention, only a small amount of formic acid suffices to adjust the pH of the solution since the decomposition of pentaerythritol formals is effected under relatively moderate conditions of a pH of 4.5–5.5 and an ordinary stainless steel such as SUS 316 or SUS 316L is utilizable for apparatus used in the decomposition step.

The process of the invention is free from formation of fine crystals of pentaerythritol and lowering of the crystallization rate since the secondarily produced pentaerythritol formals are continuously decomposed and removed without accumulation at high concentration, and ensures the conversion of pentaerythritol formals into pentaerythritol, with the result that the total yield of pentaerythritol is increased by 2–3 percent and the purity of the product by 2–2.5 percent when compared to conventional processes.

By the process of the invention, highly pure pentaerythritol can be produced at a high yield, whereas the production of highly pure pentaerythritol at high yield has never been achieved by prior processes wherein the separated solution containing sodium formate is recirculated to the reaction system as it is.

In the process of the present invention wherein an aqueous solution which contains pentaerythritol and sodium formate is added with sodium hydroxide to separate sodium formate as crystals and the separated solution is recirculated to the reaction step for use as a starting solution, all or part of the reaction solution may be thermally treated or the reaction solution may be subjected to a thermal treatment wherein pentaerythritol is separated from the reaction solution without thermal treatment, the separated solution is thermally treated and sodium hydroxide is added to the solution to separate sodium formate therefrom, and the separated solution is recirculated to the reaction system. In the latter embodiment, the separated solution can be maintained with a relatively high concentration of pentaerythritol formals, so that the acid decomposition is feasible under relatively moderate conditions since it is possible to keep the decomposition rate at a high level due to the high initial concentration of the formals. As a result, though the decomposition rate of pentaerythritol formals becomes low when determined on the basis of the total amount of the formals contained in the separated solution, it will become high when determined on the basis of the amount of pentaerythritol formals secondarily and freshly produced in the reaction step.

In order to properly understand the process of the invention, it is desirable to consider a preferred embodiment according the sole FIGURE of the drawing.

To a reactor 2 are fed an acetaldehyde and formaldehyde aqueous solution through a pipe 1 and through pipe 13 a filtrate from which sodium formate in the form of crystals has been separated by filtration. The reaction solution in reactor 2 is fed to pressure distiller 4 through pipe 2 and an excess of formaldehyde is removed by distillation from pipe 5. The remaining solution is treated in the bottom of distiller 4 or in another vessel (not shown) in the pH range of 4.5–5.5 at a temperature of 120°–170°C. for decomposing pentaerythritol formals and is passed through pipe 6 to crystallizer 7 for concentration, crystallization and separation of pentaerythritol wherein the solution is separated into crystals of pentaerythritol and the pentaerythritol- and sodium formate-containing aqueous solution. The thus separated pentaerythritol crystals are withdrawn from pipe 8 and the aqueous solution from which the pentaerythritol crystals are separated is fed through pipe 9 to a salting-out crystallizer 10 into which is discharged sodium hydroxide through pipe 11 to crystallize sodium formate. The thus crystallized formate is separated by filtration and discharged through discharging tube 12 and the resultant filtrate is recirculated to the reaction step through the pipe 13 for use as part of the starting reaction solution.

EXAMPLES 1–3

30.3 kg/hr of a 30 wt. % formaldehyde aqueous solution, 1.7 kg/hr of 98 wt. % acetaldehyde, 9.1 kg/hr of a filtrate from which sodium formate has been separated and containing 20 wt. % sodium hydroxide (and 0.11 kg/hr of combined formaldehyde) and 15 kg/hr of distilled water were fed into a tube-type reactor equipped with an agitator and a cooler and incorporated in the flow system as shown in the FIGURE, and were maintained at 35°C. for 2 hours. The resultant reaction solution to which was added formic acid to adjust its pH to 6.0–6.5 contained 0.48 wt. % of combined formaldehyde and 0.16 kg/hr of combined formaldehyde was freshly secondarily produced in the reaction step. Then, the excess of formaldehyde was removed by pressure distillation. The remaining solution was treated in the bottom of the pressure distiller or in a separate vessel under the pH, time and temperature conditions indicated in the Table below. A part of the solution sampled at the outlet of the distillation vessel was subjected to analysis of the monopentaerythritol content in accordance with the method using benzaldehyde as prescribed in JIS K 1510. Simultaneously, formaldehyde combined with pentaerythritol formals was determined by the ordinary method using sodium chromotrope. As a result, the content of monopentaerythritol was found to be in the range of 88.1–88.3 mole % and the combined formaldehyde which was secondarily produced in the reaction step was found to be completely decomposed.

Then, the solution was subjected to concentration, crystallization and separation treatments to obtain mimetic crystals of pentaerythritol with sizes as large as 100–300 μ, which were easily separated from the solution. The purity of pentaerythritol was as high as 95.4–95.5 wt. %. Furthermore, the combined formal concentration of the separated solution was 1.2 wt. % and the pentaerythritol concentration was 12 wt. %.

Thereafter, the separated solution was fed into a salting-out crystallizer to which was also added sodium hydroxide to allow sodium formate to crystallize for separation. The resultant solution was recirculated for use as part of a starting reaction solution.

The test results are shown in the Table which will be described more fully hereinafter.

COMPARATIVE EXAMPLES 1–3

For Comparative Examples 1 and 2, Example 1 was repeated except that the separated solution which was obtained by adding sodium hydexide to the aqueous solution containing pentaerythritol and sodium formate was not employed as a part of a starting reaction solution but 3.8 kg/hr of 48% sodium hydroxide was used as the starting material. Additional, in Comparative Example 2, the reaction solution was thermally treated under conditions apart from those of the present invention as indicated in the Table. For Comparative Example 3, Example 1 was repeated except that the thermal treatment under such specific conditions as defined in the present invention was not effected. The test results are shown in the following Table.

Table

|  | Units | Example No. | | | Comparative Example No. | | |
|---|---|---|---|---|---|---|---|
|  |  | 1 | 2 | 3 | 1 | 2 | 3 |
| Feeding Rate to Reactor | | | | | | | |
| 30% Formaldehyde aqueous solution | kg/hr | 30.3 | 30.3 | 30.3 | 30.3 | 30.3 | 30.3 |
| 98% Acetaldehyde | kg/hr | 1.7 | 1.7 | 1.7 | 1.7 | 1.7 | 1.7 |
| 48% Sodium Hydroxide | kg/hr | — | — | — | 3.8 | 3.8 | — |
| Sodium Formate-separated filtrate alkali solution used in circulation | kg/hr | 9.1 | 9.1 | 9.1 | — | — | 9.1 |
| Water | kg/hr | 15 | 15 | 15 | 15 | 15 | 15 |
| Combined Formaldehyde in Reaction Solution | | | | | | | |
| Combined Formaldehyde | wt. % | 0.48 | 0.48 | 0.48 | 0.27 | 0.27 | 0.57 |
| Amount per hour | kg/hr | 0.27 | 0.27 | 0.27 | 0.14 | 0.14 | 0.32 |
| Formation amount of combined formaldehyde | kg/hr | 0.16 | 0.16 | 0.16 | 0.14 | 0.14 | 0.18 |
| Decomposition of Formals | | In vessel-type container | | In bottom of pressure distiller | — | Vessel-type container | — |
| Temperature | °C. | 150 | 130 | 150 | — | 150 | — |
| Time | Min. | 60 | 60 | 60 | — | 80 | — |
| pH | — | 5.1 | 4.7 | 5.1 | — | 4.2 | — |
| Decomposition amount of combined formaldehyde | kg/hr | 0.16 | 0.16 | 0.16 | — | 0.08 | — |
| Yield of monopentaerythritol | mole % | 88.3 | 88.5 | 88.1 | 85.9 | 86.1 | 85.6 |
| Pentaerythritol concentration in crystal-separated solution | wt. % | 12 | 12 | 12 | — | — | 31 |
| Size of pentaerythritol crystals | μ | 100–300 | 100–300 | 100–300 | — | — | 10–50 |
| Purity of pentaerythritol product | % | 95.5 | 95.4 | 95.5 | 94.0 | 94.5 | 93.5 |

EXAMPLE 4

Pentaerythritol was prepared in accordance with the flow system of the drawing and by using the reactor and feed charge of Example 1. In this example, however, two-thirds of the bottom solution in the pressure distiller was treated in a specific container of high temperature to decompose pentaerythritol formals and then combined with the balance of the solution for further treatment. The decomposition of pentaerythritol formals was effected at a temperature of 180°C. for a time period of 100 minutes at a pH of 4.7. As a result, the combined formaldehyde concentration in the reaction solution was 0.48 wt. %, the formation amount of combined formaldehyde was 0.16 kg/hr, the decomposition rate of combined formaldehyde was 0.16 kg/hr, the yield of monopentaerythritol was 88.3 mol %, and the purity of pentaerythritol product was 95.5 wt. %. Thus, the results were comparable to those of Example 1.

What is claimed is:

1. In a process for producing pentaerythritol wherein sodium hydroxide is added to an aqueous solution containing pentaerythritol and sodium formate to allow the sodium formate to crystallize for separation and the separated solution is recirculated for use as part of the starting reaction solution, the improvement which comprises thermally treating at least a part of the reaction solution containing pentaerythritol formals in the pH range of 4.5–5.5 at a temperature of 120°–170°C., for 20–120 minutes, crystallizing and separating the resultant pentaerythritol, adding sodium hydroxide to the separated solution which contains pentaerythritol and sodium formate to crystallize the sodium formate therefrom and separating the crystallized sodium formate.

2. The process according to claim 1 wherein the separation of pentaerythritol by crystallization is effected after the amount of pentaerythritol formals contained in the pentaerythritol-separated solution reaches less than 3.0 wt. % when expressed in terms of the concentration of combined formaldehyde.

3. The process according to claim 2 wherein said amount of pentaerythritol formals is less than 2.0 wt. %.

* * * * *